United States Patent
Minisci et al.

(10) Patent No.: US 8,420,867 B2
(45) Date of Patent: Apr. 16, 2013

(54) CATALYTIC PROCESS FOR THE PREPARATION OF HYDROPEROXIDES OF ALKYLBENZENES BY AEROBIC OXIDATION UNDER MILD CONDITIONS

(75) Inventors: Francesco Minisci, Milan (IT); Ombretta Porta, Milan (IT); Angelo Clerici, legal representative, Milan (IT); Alberto Clerici, legal representative, Milan (IT); Carlo Punta, Milan (IT); Francesco Recupero, Milan (IT); Cristian Gambarotti, Cremona (IT); Raffaele Spaccini, Papiano (IT)

(73) Assignee: Polimeri Europa S.p.A., Milan (IT)

( * ) Notice: Subject to any disclaimer, the term of this patent is extended or adjusted under 35 U.S.C. 154(b) by 128 days.

(21) Appl. No.: 12/933,190

(22) PCT Filed: Mar. 13, 2009

(86) PCT No.: PCT/EP2009/001921
§ 371 (c)(1),
(2), (4) Date: Dec. 3, 2010

(87) PCT Pub. No.: WO2009/115275
PCT Pub. Date: Sep. 24, 2009

(65) Prior Publication Data
US 2011/0082320 A1 Apr. 7, 2011

(30) Foreign Application Priority Data
Mar. 18, 2008 (IT) .............................. MI2008A0460

(51) Int. Cl.
*C07C 409/02* (2006.01)

(52) U.S. Cl.
USPC .......................................... 568/570; 568/577

(58) Field of Classification Search ................... 568/577
See application file for complete search history.

(56) References Cited

FOREIGN PATENT DOCUMENTS

WO 2008 037435 4/2008

OTHER PUBLICATIONS

U.S. Appl. No. 12/933,204, filed Sep. 17, 2010, Minisci, et al.
Fukuda, Osamu et al., "Preparation of Hydroperoxides by N-Hydroxyphthalimide-Catalyzed Aerobic Oxidation of Alkylbenezenes and Hydroaromatic Compounds and Its Application", Advanced Synthesis & Catalysis, vol. 343, pp. 809-813, XP002432348, ISSN: 1615-4150, (Jan. 1, 2001).
Sugamoto, Kazuhiro et al., Regioselective Hydroperoxygenation of Aralkanes and α, β-Unsaturated Carbonyl Compounds Catalyzed by N-Hydroxyphthalimide and 2,2'-Azobis (4-methoxy-2,4-dimethylvaleronitrile), Synthetic Communications, vol. 35, No. 14, pp. 1865-1874, XP009120109, ISSN: 0039-7911, (2005).
Sheldon, A. Roger et al., "Organocatalytic Oxidations Mediated by Nitroxyl Radicals", Advanced Synthesis & Catalysis, vol. 346, pp. 1051-1071, XP002459137, ISSN: 1615-4169, (Jan. 1, 2004).
Minisci, Francesco et al., "Molecule-induced homolysis of N-hydroxyphthalimide (NHPI) by peracids and dioxirane. A new, simple, selective aerobic radical epoxidation of alkenes", Tetrahedron Letters, vol. 47, No. 9, pp. 1421-1424, XP025003620, ISSN: 0040-4039, (Feb. 27, 2006).
Einhorn, Cathy et al., "Oxidation of organic substrates by molecular oxygen mediated by N-hydroxyphtalimide (NHPI) and acetaldehyde", Chem. Commun., pp. 447-448, XP002537081, (1997).

*Primary Examiner* — Sikarl Witherspoon
(74) *Attorney, Agent, or Firm* — Oblon, Spivak, McClelland, Maier & Neustadt, L.L.P.

(57) ABSTRACT

Process for the preparation of hydroperoxides of alkylbenzenes characterized by the fact that the alkylbenzene reacts with oxygen in the presence of a catalytic system consisting of an N-hydroxyimide associated with a peroxide activator having a peracid or dioxyrane structure, possibly generated in situ.

20 Claims, No Drawings

CATALYTIC PROCESS FOR THE PREPARATION OF HYDROPEROXIDES OF ALKYLBENZENES BY AEROBIC OXIDATION UNDER MILD CONDITIONS

FIELD OF THE INVENTION

The present invention relates to a catalytic process for the preparation of hydroperoxides of alkylbenzenes by means of aerobic oxidation under mild conditions.

More specifically, the present invention relates to a new catalytic process, which is significantly improved respect to the known art, for the aerobic oxidation in liquid phase of alkylbenzenes to hydroperoxide, industrially used for the preparation of styrene, propylene oxide, diphenols and ketones.

Significant improvements have been obtained with the use of catalysts based on N-hydroxyimides associated with peroxide activators having a dioxyrane or a peracid structure. The use of small amounts of aliphatic or aromatic aldehydes, as activators, which generate in situ the corresponding peracids necessary for the activation of the oxidation, have proved to be of particular interest. The main advantages with respect to the known art are: (i) an operative simplification related to the low reaction temperature used (30-80° C. versus 135-170° C. used in the processes previously developed); (ii) a higher selectivity to hydroperoxide (95-990); (iii) the possibility of a facilitated recovery and recycling of the catalyst, which remains unaltered at the low temperatures used, whereas the same catalyst decomposes at the higher temperatures previously adopted.

ART PRIOR TO THE INVENTION

The autoxidation of ethylbenzene to hydroperoxide (see equation 1) is an important process for the production of styrene and propylene oxide (see equation 2) (U.S. Pat. No. 3,351,635)

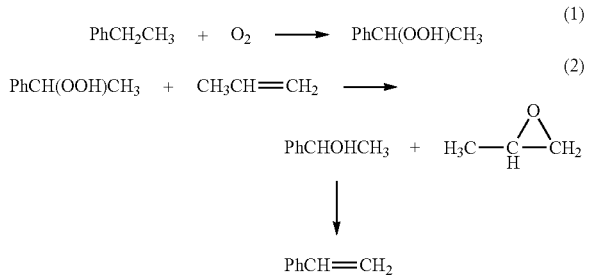

$$PhCH_2CH_3 + O_2 \longrightarrow PhCH(OOH)CH_3 \quad (1)$$

$$PhCH(OOH)CH_3 + CH_3CH{=}CH_2 \longrightarrow$$

$$PhCHOHCH_3 + H_3C\!-\!\underset{H}{C}\!\overset{O}{\!-\!}CH_2$$

$$\downarrow$$

$$PhCH{=}CH_2$$

It is well-known, on the other hand, that the hydroperoxide of cumene is the base intermediate for the production of phenol and acetone (Hock process). The request for phenol, however, is growing more rapidly than that for acetone and consequently an overproduction of acetone can be expected. Alternative methods for the production of phenol are consequently of great interest. In particular, the peroxidation of sec-butylbenzene and phenylcyclohexane seems to be of relevant interest because, together with phenol, industrially interesting ketones are obtained, such as methyl ethyl ketone, cyclohexanone, cyclooctanone and cyclododecanone.

The most delicate phase of the whole process is the production of hydroperoxide. Non-catalyzed autoxidation is a radical chain process in which the hydroperoxide, generated in situ, acts in turn as radical chain initiator. With respect to the autoxidation of cumene, widely used for the production of phenol, ethylbenzene is less reactive and requires higher temperatures which favour both the decomposition of the hydroperoxide and its further oxidation (I. Hermans et al. J. Org. Chem. 2007, 72, 3057). The lower are the temperatures and the conversion, the higher will be the selectivity of the latter (U.S. Pat. No. 3,459,810).

The autoxidation in liquid phase of ethylbenzene was carried out in the presence of base substances, such as carbonates or oxides of alkaline or alkaline-earth metals, in order to neutralize the acid by-products of the reaction. The latter, which are formed at high temperatures, catalyze the decomposition of the hydroperoxide reducing the selectivity and at the same time leading to the formation of small amounts of phenol which inhibit the oxidation (U.S. Pat. Nos. 2,867,666, 3,592,857, 4,158,022).

More recently, it was found that N-hydroxyimides catalyze the aerobic oxidation of hydrocarbons (Y. Ishii et al. Adv. Synth. Catal. 2001, 343, 393; F. Minisci et al. J. Mol. Catal. 2003, 204-205, 63; F. Recupero, C. Punta Chem. Rev. 2007, 107, 3800-3842) and attempts were made to also use this type of catalysis for the synthesis of the hydroperoxide of ethylbenzene and other alkylbenzenes of industrial interest.

In a recent patent (EP 1,520,853 A1), it is reported that the hydroperoxide of ethylbenzene can be obtained by oxidation with oxygen, catalyzed by N-hydroxyimides in the presence of alkaline metal derivatives (hydroxides, oxides, salts). The selectivities to hydroperoxide indicated in this patent vary from 50 to 70% with conversions ranging from 10 to 17% operating at a temperature of 148° C.

It has been recently found that peracids and dioxyranes, associated with N-hydroxyimides, have a considerable activity for the production of cumene hydroperoxide with a high selectivity by the aerobic oxidation of cumene under very mild conditions (Minisci et al. PCT/EP07/008,341).

The Applicants have now found that these catalytic systems are also efficient in the peroxidation of alkylbenzenes, less reactive than cumene, such as ethylbenzene, sec-butylbenzene and phenylcyclohexane.

DESCRIPTION OF THE INVENTION

The present invention, described in the enclosed claims, relates to the use of new catalytic systems which allow the oxidation of alkylbenzenes to hydroperoxides with oxygen under mild temperature and pressure conditions, with higher selectivities with respect to the industrial processes currently adopted, which operate at much higher temperatures.

The catalytic systems, relating to the present invention, consist of an N-hydroxy-derivative activated with a peroxide derivative having a peracid (RCOOOH) or a dioxyrane $R_2C$ (OO) structure, used as such or generated "in situ" during the oxidation. It should be pointed out that the use of only one of the two components leads to lower overall yields in hydroperoxide with respect to those obtained with the two components simultaneously present. Furthermore, the hydroperoxides of alkylbenzenes produced by the reaction, associated with an N-hydroxyimide, are not capable of catalyzing the oxidation itself under the reaction conditions.

The behaviour of peracids and dioxyranes is completely different with respect to the classical radical initiators claimed in other circumstances (Adv. Synth. Catal. 2001, 243, 809; Adv. Synth. Catal. 2004, 246, 1051; U.S. Pat. No. 6,720,462) in which the thermal decomposition of other peroxides or azo-derivatives produces radicals, which start the radical chains of the oxidation catalyzed by N-hydroxyimides. Actually, peracids and dioxyranes are stable at the same reaction temperatures and do not produce radicals by spontaneous decomposition, but they react with N-hydroxy-derivatives generating nitroxide radicals which are responsible for peroxidation with oxygen (Minisci et al. Tetrahedron Letters 2006, 47, 1421).

With respect to the well-known peroxidation of cumene, at the base of the industrial production of phenol, that of ethylbenzene has greater difficulties for two basic reasons: (i) the secondary C—H benzyl bond of ethylbenzene is less reactive than the tertiary C—H benzyl bond of cumene (F. Minisci et al. J. Mol. Catal. 2003, 204-205, 63) and above all the hydroperoxide of cumene does not have further reactive C—H bonds, whereas the hydroperoxide of ethylbenzene has a tertiary C—H benzyl bond which is more reactive than the secondary C—H one of the starting ethylbenzene (I. Hermans et al. J. Org. Chem. 2007, 72, 3057). Consequently, increasing the concentration of hydroperoxide, the latter prevalently reacts creating secondary products (mainly acetophenone), which drastically reduce the selectivity. At high oxidation temperatures, on the other hand, as indicated in previous patents (U.S. Pat. Nos. 2,867,666, 3,459,810, 3,592,857 and 4,158,022) the hydroperoxide of ethylbenzene partially decomposes contributing to reduce further the selectivity.

Alkylbenzenes with more hyndered alkyl groups respect to isopropyl are also less reactive than cumene in aerobic peroxidation, mainly for steric reasons and they therefore require higher reaction temperatures with a consequent lower selectivity.

The use of catalytic systems, according to the present invention, on the one hand allows to work at much lower temperatures, which avoid the thermal decomposition of the hydroperoxide, and on the other attenuates the reactivity difference between the hydroperoxide and the starting alkylbenzene, leading to a considerable increase in the selectivity (>95% for conversions of 15-20%).

Among N-hydroxy-derivatives, N-hydroxyimides, in particular N-hydroxyphthalimides, easily accessible from cheap industrial products such as phthalic anhydride and its derivatives, are of great interest as catalysts. N-hydroxyphthalimide, as such, has a modest catalytic activity for aerobic oxidation in the absence of solvents as it has a low solubility in alkylbenzenes at the reaction temperature. It is sufficient, however, to use moderate amounts of polar solvents, such as acetonitrile or acetone, resistant to aerobic oxidation under the reaction conditions, to dissolve the small quantities of N-hydroxyphthalimide necessary for having a good catalytic activity.

The N-hydroxyphthalimide, which remains unchanged during the reaction, can be easily recovered at the end of the oxidation by crystallization from the reaction mixture, after removing the polar solvent by distillation. The small quantity of remaining catalyst is extracted with water from the residual solution. The oxidation of alkylbenzenes, however, can also be effected without solvents, by modifying the structure of the N-hydroxyphthalimide with the introduction of an alkyl chain which increases its lipophilic nature and makes the catalyst sufficiently soluble, allowing an effective catalytic activity without the necessity of using solvents.

In order to exert a good catalytic activity, as claimed in the present invention, the N-hydroxyphthalimides require the presence of small quantities of activators consisting of peracids or dioxyranes. The latter can be used as such or with precursors, such as aliphatic or aromatic aldehydes for peracids and ketones with potassium monopersulfate for dioxyranes. The most convenient activators are aldehydes which, under the operating conditions, are slowly oxidized to peracids by the oxygen, whereas ketones require the presence of monopersulfate to generate dioxyranes. A previous attempt using N-hydroxyphthalimides associated with aldehydes in the aerobic oxidation of alkyl aromatic compounds did not lead to any traces of hydroperoxides (Chem. Commun. 1997, 447).

The oxidation is preferably carried out at temperatures ranging from 30 to 80° C. operating with quantities of N-hydroxy-derivative preferably ranging from 0.2% to 5% in moles with respect to the alkylbenzene (substrate).

The quantities of aldehydes used as precursors of the activators generated in situ preferably range from 0.2% to 10% in moles. In order to obtain selectivities in hydroperoxide >90%, it is convenient to maintain the conversions of alkylbenzene <30%.

Some examples are provided for illustrative purposes, which however in no way limit the potentiality of the process claimed by the present invention.

Example 1

A solution of 200 mmoles (25 ml) of ethylbenzene, 4 mmoles of acetaldehyde and 4 mmoles of N-hydroxyphthalimide in 25 ml of acetonitrile is stirred for 6 hours at 60° C. in an atmosphere of oxygen at ordinary pressure. $^1$H-NMR and HPLC analyses show a ethylbenzene conversion of 15% with a selectivity in hydroperoxide of 97%. The only by-product present in a significant quantity is acetophenone (<3%), whereas the N-hydroxyphthalimide is easily recovered and recycled by distilling the acetonitrile, which is reused, and extracting with water the residual solution of hydroperoxide in ethylbenzene.

Example 2

The procedure showed in Example 1 is adopted without N-hydroxyphthalimide. The ethylbenzene conversion is of 15% with a selectivity of 30% to hydroperoxide, 40% to acetophenone and 30% in alcohol.

Example 3

The procedure showed in Example 1 is adopted without acetaldehyde. The ethylbenzene conversion is <5%.

Example 4

The procedure showed in Example 1 is adopted using propionaldehyde instead of acetaldehyde. The ethylbenzene conversion is of 16% with a selectivity of 97% in hydroperoxide and 3% in acetophenone.

Example 5

The procedure showed in Example 1 is adopted at 80° C., using benzaldehyde instead of acetaldehyde. The ethylbenzene conversion is of 17%, with a selectivity in hydroperoxide and acetophenone of 95% and 5% respectively.

Example 6

A solution of 40 mmoles of ethylbenzene, 0.4 mmoles of N-hydroxyphthalimide and 4 mmoles of benzaldehyde in 5 ml of acetone is stirred for 6 hours at 68° C. in an atmosphere of oxygen at ordinary pressure. The ethylbenzene conversion is of 11% with a selectivity of 87% in hydroperoxide and 13% in acetophenone.

Example 7

A solution of 2% of lauryl ester of 4-carboxylic acid of N-hydroxyphthalimide and 2% of propionaldehyde in 5 ml of ethylbenzene is stirred for 24 hours at 60° C. in an atmosphere of oxygen at ordinary pressure. The ethylbenzene conversion is of 11%, with a selectivity in hydroperoxide and acetophenone of 90% and 10% respectively.

Example 8

A solution of 200 mmoles (25 ml) of ethylbenzene and 4 mmoles of N-hydroxyphthalimide in 25 ml of acetonitrile is stirred for 6 hours at 60° C. in an atmosphere of oxygen at ordinary pressure. The ethylbenzene conversion is of 11% with a selectivity in hydroperoxide and acetophenone of 92% and 8% respectively.

Example 9

A solution of 64.3 mmoles (10 ml) of sec-butylbenzene, 3.12 mmoles of propionic aldehyde and 0.64 mmoles of N-hydroxyphthalimide in 3.75 ml of acetonitrile is stirred for 24 hours at 70° C. in an atmosphere of oxygen at ordinary pressure. $^1$H-NMR and HPLC analyses show a conversion of sec-butylbenzene of 21% with a selectivity in hydroperoxide of 97%. The only by-product present is 2-phenyl-2-butanol (3%). The acetonitrile is distilled and the unaltered N-hydroxyphthalimide mostly precipitates and is recovered by filtration. A smaller part of the catalyst is recovered by extraction with water from the residual solution of sec-butylbenzene. A total of 90% of the catalyst is recovered.

Example 10

The same procedure is adopted as in Example 9 using phenyl cyclohexane instead of sec-butylbenzene. The conversion is 17% with a selectivity in hydroperoxide of 99%. 90% of unaltered N-hydroxyphthalimide is recovered.

The invention claimed is:

1. A process for the preparation of a hydroperoxide of an alkylbenzene selected from the group consisting of ethylbenzene, sec-butylbenzene and a cyclo-alkylbenzene, comprising:
   reacting the alkylbenzene with oxygen in the presence of a catalytic system consisting of an N-hydroxyimide and at least one peroxide activator selected from the group consisting of a peracid and a dioxirane.

2. The process according to claim 1, wherein the N-hydroxyimide is N-hydroxyphthalimide and the reacting is carried out in the presence of at least one solvent selected from the group consisting of acetonitrile, acetone and dimethyl carbonate, in which the N-hydroxyimide is soluble.

3. The process according to claim 1, wherein the catalyst consists of an alkyl-derivative of N-hydroxyphthalimide and the reacting is carried out in the absence of solvents.

4. The process according to claim 1, wherein the peroxide activator is a peracid generated in situ during the reacting from a corresponding aliphatic or aromatic aldehyde.

5. The process according to claim 1, wherein the temperature during the reacting is from 30° C. to 80° C.

6. The process according to claim 1, wherein the quantity of N-hydroxyimide is from 0.2% to 10% in moles with respect to the alkylbenzene.

7. The process according to claim 1, wherein the peracids or dioxirane are present in quantities ranging from 0.1% to 5% in moles with respect to the alkylbenzene.

8. The process according to claim 4, wherein the aliphatic or aromatic aldehyde is present in an amount of from 0.5% to 10% in moles with respect to the alkylbenzene.

9. The process according to claim 1, wherein the reacting converts from 10% to 30% of the alkylbenzene to a hydroperoxide.

10. The process according to claim 1, where the alkylbenzene is ethylbenzene.

11. The process according to claim 1, wherein the alkylbenzene is sec-butylbenzene.

12. The process according to claim 1, wherein the alkylbenzene is a cyclo-alkylbenzene.

13. The process according to claim 1, wherein the alkylbenzene is at least one selected from the group consisting of ethylbenzene, sec-butylbenzene and phenyl cyclohexane, and the catalytic system consists of N-hydroxyphthalimide and a peracid of at least one selected from the group consisting of acetaldehyde, propionaldehyde, and benzaldehyde.

14. The process according to claim 13, wherein from 11 to 21% of the alkylbenzene is converted to a hydroperoxide of the alkylbenzene with a selectivity of 87-99%.

15. A process for forming an alkylbenzene hydroperoxide, comprising:
   reacting an alkylbenzene with oxygen in the presence of a catalytic system comprising an N-hydroxyimide and at least one peroxide activator selected from the group consisting of a peracid and a dioxirane,
   wherein the alkylbenzene is at least one selected from the group consisting of ethylbenzene, sec-butylbenzene and a cyclo-alkylbenzene.

16. The process according to claim 15, wherein after the reacting the hydroxyimide is recovered in an amount of at least 90% based on the total amount of the N-hydroxyphthalimide present during the reacting.

17. The process according to claim 15, further comprising:
   forming the peracid concurrently during the reacting.

18. The process according to claim 15, wherein the reacting is carried out in the presence of a solvent selected from the group consisting of an acetonitrile, acetone and a dimethyl carbonate.

19. The process according to claim 15, wherein the temperature during the reacting is from 30 to 80° C.

20. The process according to claim 1, wherein after the reacting the hydroxyimide is recovered in an amount of at least 90% based on the total amount of the N-hydroxyphthalimide present during the reacting.

* * * * *